United States Patent
Gara et al.

(10) Patent No.: US 11,753,417 B2
(45) Date of Patent: Sep. 12, 2023

(54) SYNTHESIS OF 14-METHYL-16-OXABICYCLO[10.3.1] HEXADEC-12-ENE

(71) Applicant: International Flavors & Fragrances Inc., New York, NY (US)

(72) Inventors: Mohamad Gara, Jatt Village (IL); Yigal Becker, Tel-Aviv (IL)

(73) Assignee: International Flavors & Fragrances Inc., New York, NY (US)

( * ) Notice: Subject to any disclaimer, the term of this patent is extended or adjusted under 35 U.S.C. 154(b) by 295 days.

(21) Appl. No.: 17/423,146

(22) PCT Filed: Jan. 16, 2020

(86) PCT No.: PCT/US2020/013845
§ 371 (c)(1),
(2) Date: Jul. 15, 2021

(87) PCT Pub. No.: WO2020/150454
PCT Pub. Date: Jul. 23, 2020

(65) Prior Publication Data
US 2022/0127278 A1    Apr. 28, 2022

Related U.S. Application Data

(60) Provisional application No. 62/793,569, filed on Jan. 17, 2019.

(51) Int. Cl.
*C07D 493/08* (2006.01)

(52) U.S. Cl.
CPC .................................. *C07D 493/08* (2013.01)

(58) Field of Classification Search
CPC ..................................................... C07D 493/08
See application file for complete search history.

(56) References Cited

U.S. PATENT DOCUMENTS

2017/0362153 A1* 12/2017 Tanino .................... C07B 61/00

FOREIGN PATENT DOCUMENTS

WO    WO-2018011386 A1 *  1/2018 ............. C07C 45/61

* cited by examiner

*Primary Examiner* — Susanna Moore

(57) ABSTRACT

Disclosed is a scalable process for preparation of 14-methyl-16-oxabicyclo[10.3.1]hexadec-12-ene (BCE), a key intermediate for manufacture of fragrance ingredient 3-methyl-cyclopentadecenone (MUSCENONE®) and analogs through reaction of 3-Methyl-1,5-cyclopentadecanedione (MCPD) and analogs with a metal or metalloid alkoxide in high yield and purity.

20 Claims, No Drawings

SYNTHESIS OF 14-METHYL-16-OXABICYCLO[10.3.1] HEXADEC-12-ENE

CROSS-REFERENCE TO RELATED APPLICATIONS

This application represents a national filing under 35 U.S.C. 371 of International Application No. PCT/US2020/013845 filed Jan. 16, 2020, and claims priority of U.S. Provisional Application No. 62/793,569 filed Jan. 17, 2019, the contents of both applications are incorporated herein by reference in their entirety for all purposes.

FIELD OF THE INVENTION

The present invention is related to the field of fragrance compounds and to their commercial scale synthesis.

BACKGROUND OF THE INVENTION

14-Methyl-16-oxabicyclo[10.3.1]hexadec-12-ene (BCE) and its isomers are useful intermediates for the preparation of fragrance ingredients dehydromuscone (MUSCENONE®) and muscone.

U.S. Pat. No. 4,480,107A describes the cyclodehydrogenation-dehydration of 3-methyl-1,5-cyclopentadecanediol (DIOL) by gradually adding the DIOL to Raney copper catalyst held at 160-165° C./20 Torr. The yield of BCE was 78.9% and the purity was 90%. See Scheme I, below.

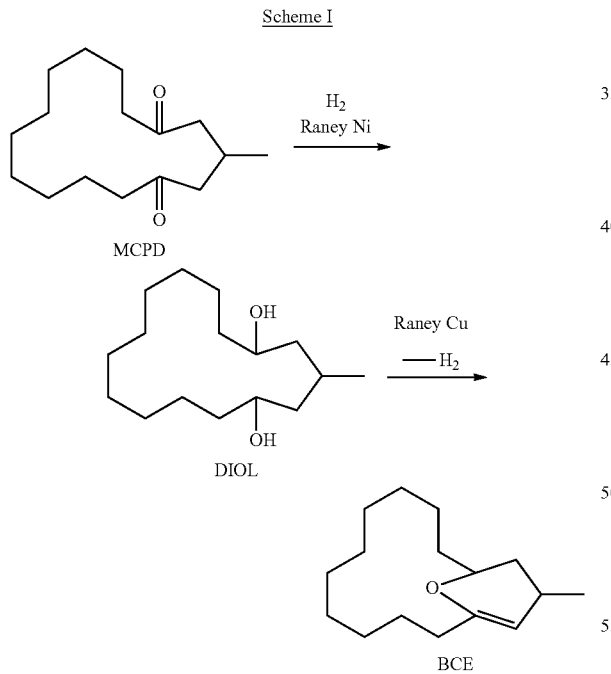

WO 2017/089327A1 describes cyclodehydrogenation-dehydration of the DIOL by heating in the presence of Raney copper catalyst suspended in 1-hexadecanol, which has a vapor pressure between that of the DIOL and BCE. The produced BCE was continuously distilled out of the reaction mixture as it was formed thus minimizing the formation of a hydrogenated byproduct, 14-methyl-16-oxabicyclo[10.3.1]hexadecane. The yield of BCE was 80% and the purity was 92-93.7%. The process can be run continuously.

The DIOL was prepared by hydrogenation of 3-methyl-1,5-cyclopentadecanedione (MCPD) in presence of Raney nickel.

According to WO 2017/050713A1, the DIOL can also be prepared in 2 steps from 14-methylbicyclo[10.3.0][1(12)]pentadecene by ozonolysis to give 14-methyl-16,17,18-trioxatricyclo[10.3.2.11,12]octadecane which is hydrogenolyzed in 80% yield using hydrogen in presence of molybdenum-doped Raney nickel. The primary disadvantage of preparing the DIOL as disclosed in WO 2017/050713A1 is the application of an ozonolysis reaction, which is considered hazardous and inappropriate for commercial scale use. Further, the intermediate ozonide (14-methyl-16,17,18-trioxatricyclo-[10.3.2.11,12]octadecane) may be explosive, and its subsequent hydrogenolysis requires the use of the expensive molybdenum-doped Raney nickel catalyst. See Scheme II.

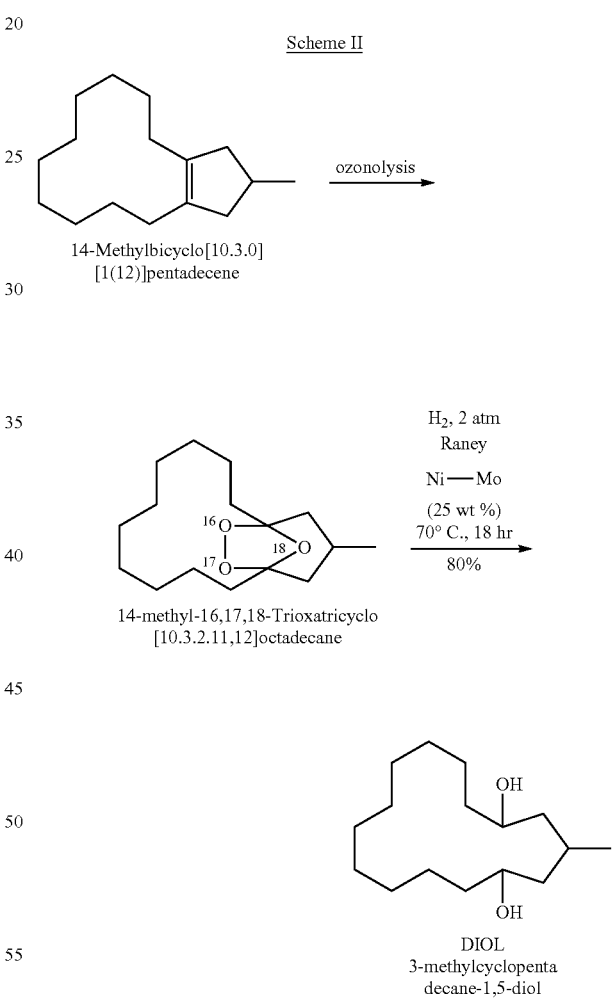

The main disadvantage of both U.S. Pat. No. 4,480,107A and WO 2017/089327A1 is that MCPD must be converted to BCE in two steps via the intermediate DIOL. The dehydrogenation-dehydration of the DIOL to BCE requires the use of expensive Raney copper catalyst and a prolonged reaction time. Furthermore, the dehydrogenation generates hydrogen gas which reduces much of BCE to a useless byproduct, 14-methyl-16-oxabicyclo[10.3.1]hexadecane (saturated BCE). See Scheme III.

Scheme III

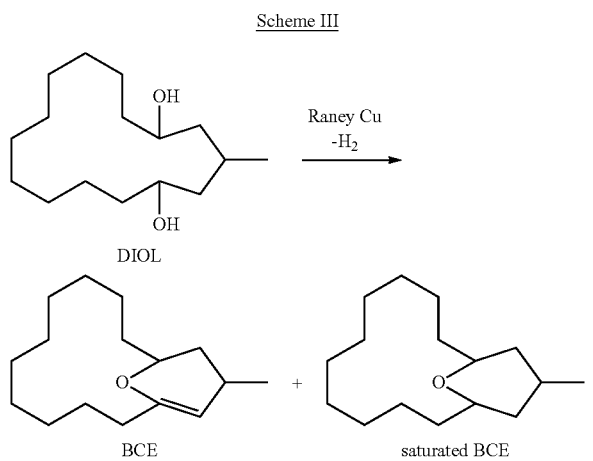

WO 2017/089327A1 teaches that in order to minimize the formation of 14-methyl-16-oxabicyclo[10.3.1]hexadecane, 1-hexadecanol is added as a solvent while BCE must be distilled off as it is formed. Subsequently 1-hexadecanol is recycled, complicating the process since it has a very high boiling point (344° C./760 mmHg).

WO 2018/011386A1 describes a process whereby MCPD is partially reduced by sodium borohydride to give a mixture of BCE, 5-Hydroxy-3-methylcyclopentadecanone (KETOL), DIOL and unreacted MCPD. See Scheme IV.

Scheme IV

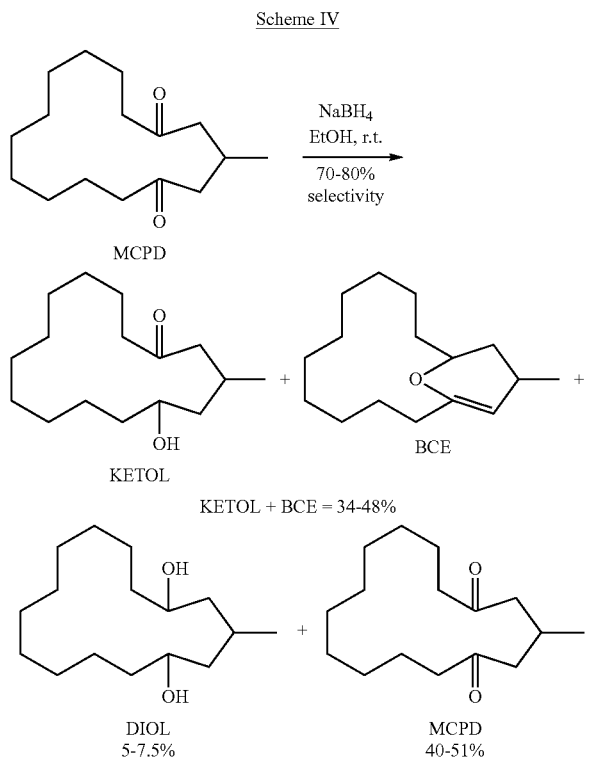

At 60% conversion of MCPD the selectivity to BCE and KETOL is 79.8%. After treating the reaction mixture with 80% phosphoric acid in toluene under reflux, the yield of 3-methylcyclopentadecenone is 32% based on MCPD. The yield can be increased to 50% if the unreacted MCPD is recovered and reused. This yield is not cost effective.

Therefore, there is a need for a new and simple economic process that converts MCPD to BCE directly and in a high yield without these disadvantages.

SUMMARY OF THE INVENTION

It has now been found that the aforementioned disadvantages are overcome by the one-step, direct conversion of MCPD to BCE in presence of a metal or metalloid alkoxide in an inert solvent, as shown in Scheme V below. BCE is the major product, accompanied by a trace amount of iso-BCE, a BCE isomer. Both BCE and iso-BCE can be readily converted to dehydromuscone (MUSCENONE®) upon treatment with acid.

Scheme V

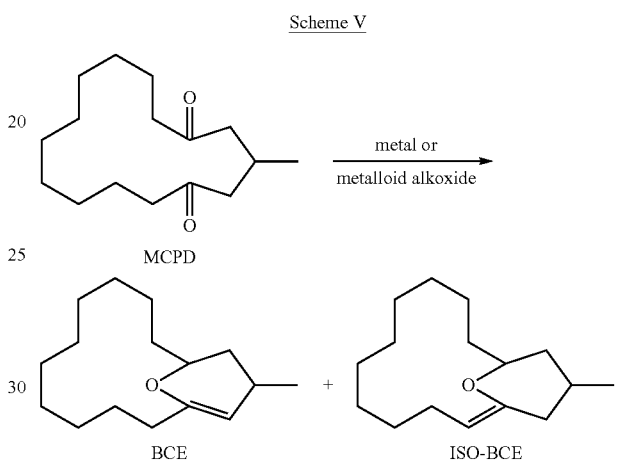

One aspect of the invention is directed to a process for preparing 14-methyl-16-oxabicyclo[10.3.1]hexadec-12-ene (BCE), comprising the steps of a) reacting 3-methyl-1,5-cyclopentadecanedione (MCPD) with a $C_1$-$C_4$ alkoxide of a metal or metalloid selected from the group consisting of sodium, magnesium, aluminum, boron, tin, zirconium and lanthanides, in an inert organic solvent and at a temperature above 80° C. to form a reaction mixture, which generates an alcohol as a side product; and b) treating the reaction mixture with an aqueous mineral acid. The process can further comprise isolating the product, BCE, through extraction and/or distillation.

In a particular embodiment, the invention is directed to a process for preparing BCE, comprising the steps of a) reacting MCPD with aluminum sec-butoxide in toluene at a temperature between 80° C. and 110° C. to form a reaction mixture, b) treating the reaction mixture with hydrochloric acid; and c) isolating the product, BCE, through extraction and distillation.

In another aspect, the invention provides a method of preparing an oxabicycloalkene compound of formula (II) and/or (III), especially (II):

Scheme VI

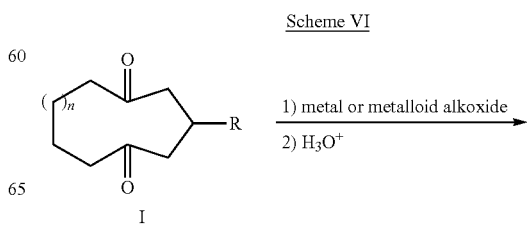

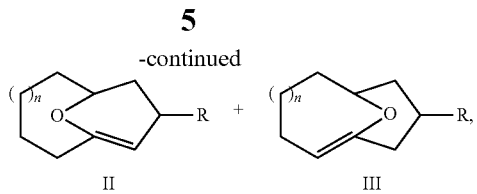

the method comprising the steps of a) reacting a cycloalkane-1,5-dione compound of formula (I) with an alkoxide of a metal or metalloid selected from the group consisting of sodium, magnesium, aluminum, boron, tin, zirconium, and lanthanides, in an inert organic solvent at an elevated temperature to form a reaction mixture; and b) treating the reaction mixture with an acidic aqueous solution;

wherein R is a $C_1$-$C_{10}$ alkyl, preferably $C_1$-$C_6$ alkyl, more preferably $C_1$-$C_4$ alkyl, and most preferably methyl or ethyl; and n is an integer selected from 4 to 10, preferably 4 to 8, more preferably 4 to 7, and most preferably 7.

The process can further comprise isolating the product of formula (II) and/or (III), through extraction and/or distillation, in particular the product of formula (II).

In the processes disclosed herein, preferably more than one molar equivalent of metal or metalloid alkoxide is present relative to MCPD or the cycloalkane-1,5-dione compound of formula (I). The molar equivalent range of metal or metalloid alkoxide can be 1 to 3 equivalents. Preferably the molar equivalent range of metal or metalloid alkoxide is 1.5 to 1.8. More preferably 1.67 molar equivalents of the metal or metalloid alkoxide are present. The metal alkoxide of the process is preferably an aluminum alkoxide. The aluminum alkoxide is preferably aluminum sec-butoxide.

The process is preferably performed at a temperature between 80° and 110° C. The inert organic solvent of the process is preferably toluene. The aqueous mineral acid of the process is preferably aqueous hydrochloric acid, preferably hydrochloric acid at a concentration of 20-23%.

DETAILED DESCRIPTION OF THE INVENTION

It has now been found that the disadvantages of the literature methods are overcome by the one-step, direct conversion of MCPD to BCE in presence of a metal or metalloid alkoxide in inert solvent, as shown in Scheme V, above. The major product is 14-methyl-16-oxabicyclo[10.3.1]hexadecane (BCE), accompanied by traces of its isomer 14-methyl-16-oxabicyclo[10.3.1]hexadec-1-ene (ISO-BCE). Both BCE and iso-BCE are readily transformed to dehydromuscone (MUSCENONE®) by acid treatment.

A great number of metal or metalloid alkoxides which are commercially available can be used in the process. Useful metal or metalloid alkoxides include, without limitation, the methoxides, ethoxides, propoxides, iso-propoxides, butoxides, iso-butoxides, sec-butoxides and tert-butoxides of metals such as sodium, magnesium, aluminum, boron, tin, lanthanides and zirconium. Preferred alkoxides include ethoxides, iso-propoxides, and sec-butoxides. Preferably the metal or metalloid alkoxide dissolves in the inert solvent selected for the reaction. Superior results are obtained with an aluminium alkoxide, as shown in Scheme VII, below. The reaction is performed by heating MCPD in presence of excess aluminum alkoxide in an inert organic solvent at elevated temperature to completely convert the MCPD to BCE with high selectivity.

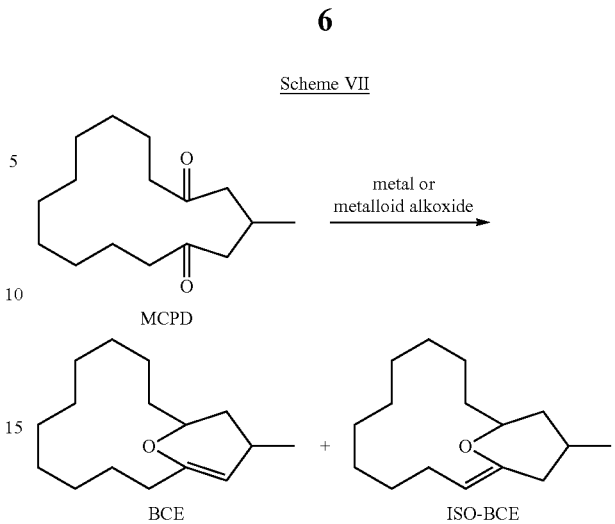

The aluminum alkoxide is used in excess of the stoichiometric amount relative to MCPD. The preferred molar range for the aluminum alkoxide is 1 to 3 molar equivalents. A particularly preferred range is 1.5 to 1.8 molar equivalents. More particularly 1.67 molar equivalents of aluminum alkoxide are preferred.

The aluminum alkoxide can be selected from aluminum methoxide, aluminum ethoxide, aluminum iso-propoxide, aluminum butoxide, aluminum sec-butoxide and aluminum tert-butoxide. Preferably, it is aluminum iso-propoxide and aluminum sec-butoxide. Aluminum sec-butoxide is particularly preferred since it is liquid at room temperature thus is easy to handle.

The inert solvent can be selected from aliphatic and aromatic hydrocarbons, and aliphatic and aromatic halohydrocarbons. Typical commercially available inert solvents include, without limitation, hexane, heptane, isooctane, toluene, xylene, dichloroethane, chlorobenzene and 1,2-dichlorobenzene. Toluene is preferred.

The preferred temperature range for any of the reactions above is from 80° C. to 110° C. under an atmospheric pressure. A particularly preferred range is from 90° C. to 95° C. For example, when aluminum isopropoxide is used as the metal alkoxide, isopropyl alcohol is produced.

The reaction mixture is worked up by adding to it an aqueous mineral acid, such as hydrochloric acid (HCl), sulfuric acid and phosphoric acid. A preferred mineral acid is aqueous HCl at a concentration of 15% to 25%. A particularly preferred HCl concentration is 20 to 23% which allows sharp phase separations.

KETOL is first formed at the working up step and then converted to BCE in the acidic condition, with iso-BCE as the side product:

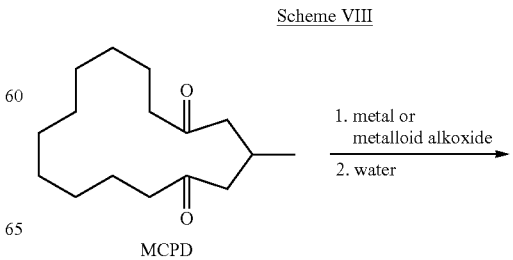

-continued

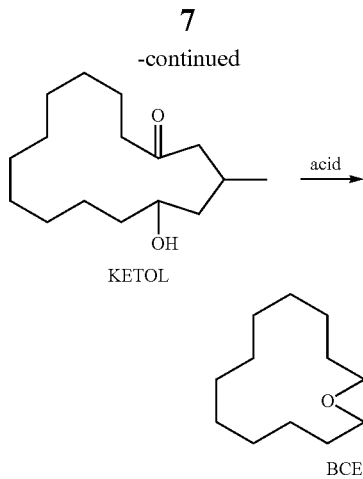

KETOL

↓ acid

BCE

In summary, one aspect of the invention is directed to a process for preparing BCE, comprising the steps of a) reacting MCPD with a $C_1$-$C_4$ alkoxide of a metal or metalloid selected from the group consisting of sodium, magnesium, aluminum, boron, tin, zirconium and lanthanides, in an inert organic solvent and at a temperature of 80° C. and above, 85° C. and above, or 90° C. and above to form a reaction mixture; and b) hydrolyzing the reaction mixture with an aqueous mineral acid. The process can further comprise isolating the product, BCE.

In the process, preferably more than one molar equivalent of metal or metalloid alkoxide is present. The molar equivalent range of metal or metalloid alkoxide can be 1 to 3 equivalents, or 1 to 2.5 equivalents, or 1 to 2 equivalents, or 1.5 to 2 equivalents relative to MCPD or the cycloalkane-1,5-dione compound of formula (I). Preferably the molar equivalent range of metal or metalloid alkoxide is 1.5 to 1.8. More preferably 1.67 molar equivalents of the metal or metalloid alkoxide are present. The metal alkoxide of the process is preferably an aluminum alkoxide. The aluminum alkoxide is preferably aluminum sec-butoxide or aluminum iso-propoxide.

The process is preferably performed at the reflux temperature of an azeotroping solvent mixture. The process is preferably performed at a temperature between 80° C. and 110° C., or between 85° C. and 100° C., or between 90° C. and 95° C., or between 90° C. and 110° C., or between 85° C. and 105° C. The inert organic solvent is preferably toluene. The aqueous mineral acid is preferably aqueous hydrochloric acid, preferably hydrochloric acid at a concentration of 20% to 23%.

In one embodiment, the invention is directed to a process for preparing BCE, comprising the steps of a) reacting MCPD with aluminum sec-butoxide in toluene at a temperature between 80° C. and 110° C., or between 85° C. and 100° C., or between 90° C. and 95° C., or between 90° C. and 110° C., or between 85° C. and 105° C. to form a reaction mixture, and b) hydrolyzing the reaction mixture with a 20% to 23% hydrochloric acid aqueous solution.

The process can further comprise isolating the product, BCE, through extraction and/or distillation. In the process, preferably more than one molar equivalent of aluminum sec-butoxide is present. The molar equivalent range of aluminum sec-butoxide is 1 to 3 equivalents, or 1 to 2.5 equivalents, or 1 to 2 equivalents, or 1.5 to 2 equivalents; preferably 1.5 to 1.8 equivalents relative to MCPD or the cycloalkane-1,5-dione compound of formula (I). More preferably 1.67 molar equivalents of aluminum sec-butoxide is present.

In another aspect, the present invention provides a method of preparing an oxabicycloalkene compound of general formula (II) or (III), especially (II), the method comprising the steps of a) reacting a cycloalkane-1,5-dione compound of formula (I) with an alkoxide of a metal or metalloid selected from the group consisting of sodium, magnesium, aluminum, boron, tin, zirconium, and lanthanides, in an inert organic solvent at an elevated temperature to form a reaction mixture; and b) treating the reaction mixture with an acidic aqueous solution:

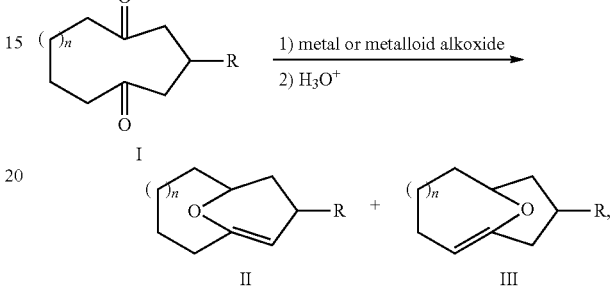

wherein R is a $C_1$-$C_{10}$ alkyl, preferably $C_1$-$C_6$ alkyl, more preferably $C_1$-$C_4$ alkyl, and most preferably methyl or ethyl;

n is an integer selected from 4 to 10, preferably 4 to 8, more preferably 4 to 7, and most preferably 7.

The metal alkoxide used in the process is preferably an aluminum alkoxide. The aluminum alkoxide is preferably aluminum sec-butoxide or aluminum iso-propoxide.

The process can further comprise isolating the product of formula (II) and/or (III), through extraction and/or distillation, in particular the product of formula (II).

In still another aspect, the invention provides a method of preparing an oxabicycloalkene compound of formula (V) and/or (VI), especially (V) from a compound of formula (IV):

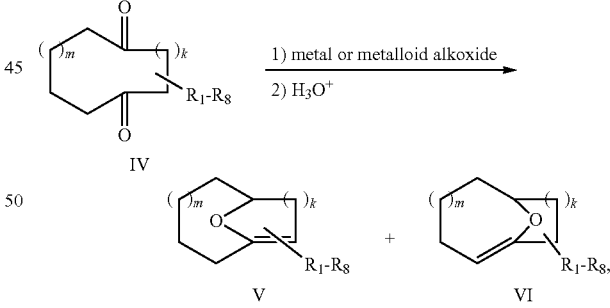

the method comprising the steps of a) reacting a cycloalkanedione compound of formula (IV) with an alkoxide of a metal or metalloid selected from the group consisting of sodium, magnesium, aluminum, boron, tin, zirconium, and lanthanides, in an inert organic solvent at an elevated temperature to form a reaction mixture; and b) treating the reaction mixture with an acidic aqueous solution;

wherein each of $R_1$ to $R_8$, individually and directly bonded to the ring of the compound of formula (IV), (V), and (VI), is H or a $C_1$-$C_{10}$ alkyl, preferably $C_1$-$C_6$ alkyl, more preferably $C_1$-$C_4$ alkyl, and most preferably methyl or ethyl;

m is an integer selected from 4 to 10, preferably 4 to 8, more preferably 4 to 7, and most preferably 7; and k is 1, 2, 3, or 4.

Each of $R_1$ to $R_8$ can be bonded to any carbon atom on either of the two rings of the compound of formula (IV), (V), and (VI).

The process can further comprise isolating the product of formula (V) and/or (VI), through extraction and/or distillation, in particular the product of formula (V).

Exemplary compounds of formula (V) are shown below:

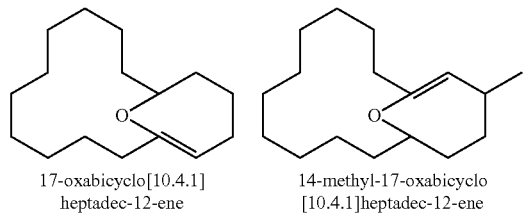

17-oxabicyclo[10.4.1] heptadec-12-ene 14-methyl-17-oxabicyclo [10.4.1]heptadec-12-ene

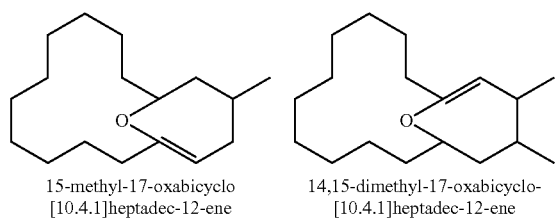

15-methyl-17-oxabicyclo [10.4.1]heptadec-12-ene 14,15-dimethyl-17-oxabicyclo-[10.4.1]heptadec-12-ene An exemplary compound of formula (VI) is shown below:

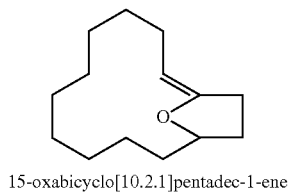 [SMILES: C1=C2\CCC(CCCCCCCCC/1)O2]

15-oxabicyclo[10.2.1]pentadec-1-ene

Other conditions and procedures described above and/or in the Examples below are applicable and/or adaptable to the process of preparation herein.

EXAMPLES

The following examples serve to illustrate the invention, without restricting it in any way.

Example 1. Preparation of 14-methyl-16-oxabicyclo [10.3.1]hexadec-12-ene (BCE) Using Aluminum Iso-Propoxide Aluminum iso-propoxide (136 g), MCPD (100 g) and toluene (200 g) were charged into a reactor equipped with a mechanical stirrer, a reflux condenser, and a thermometer. Under constant stirring, the mixture was heated to 93° C. with gentle reflux. Heating was continued for 6 to 7 hours. At this stage the reaction mixture consisted of <0.5% MCPD, iso-BCE <2.5% and BCE >85%. The reaction mixture was cooled to 50° C. Toluene (400 g) was added followed by slow addition of 350 g of 23% aqueous HCl at 50° C. The mixture was allowed to stir for 30 minutes at 40° C. The aqueous HCl phase was removed. The organic phase was washed at 45° C. with 200 g of 5% aqueous NaOH. The aqueous NaOH phase was removed. The organic phase was then washed with 200 g of a solution of 20% aqueous phosphoric acid and 9% aqueous NaCl at 50° C. for 1 hr. After the acidic aqueous phase was removed, the organic phase was washed again with 180 g of 2.4% aqueous NaCl solution (pH>6).

The resulting organic phase was distilled under atmospheric pressure to remove water (temperature ca. 93° C.). The residue was flash distilled at 160° C. to 185° C. and a vacuum of 1 mmHg to give 85 g of BCE having a purity of 93%. Yield 89-93%. IR: 1668.7 cm$^{-1}$. UV: 203 nm; MS: M+=236, (58). m/e: 221 (36), 207 (7), 194 (21), 178 (23), 165 (5), 149 (14), 135 (16), 121 (22), 109 (44), 95 (71), 81 (55), 69 (100), 55 (47), 41 (29). NMR 6 ppm (CDCl$_3$): 0.95 (3H, d, J=7); 1.2-1.5 (18H, m); 1.9-2.4 (5H, m); 3.8-3.9 (1H, m); 4.3-4.4 (1H, d).

Example 2. Preparation of 14-methyl-16-oxabicyclo [10.3.1]hexadec-12-ene (BCE) Using Aluminum Sec-Butoxide To a reactor equipped with mechanical stirrer, reflux condenser, thermometer and Dean-Stark trap, aluminum sec-butoxide (974.9 g), MCPD (600 g) and toluene (2000 g) was charged. The mixture was stirred and the temperature was raised to 90-95° C. until gentle reflux was maintained while methyl ethyl ketone, sec-butanol and toluene were distilled off (head temperature 52-58° C.). Heating was continued for 3-4 hours. The reaction was judged complete when the reaction mixture consisted of <0.5% MCPD, 92.4% BCE and 4.3% iso-BCE. The reaction mixture was cooled to 30° C. and treated with a 23% aqueous HCl solution at 50° C. for 60 minutes. The organic phase was collected by removing the aqueous phase. This aqueous wash step was repeated three times with the following aqueous solutions: (1) 5% NaOH at 45° C. for 45 minutes, (2) 20% phosphoric acid at 50° C. for 1 hour, and (3) 10% sodium sulfate at 50° C. for 1 hour. Subsequently, the toluene was removed by distillation from the organic phase. The residue was flash distilled at 170-180° C./1 mmHg to give 526 g of BCE (93% yield).

Example 3. Preparation of KETOL Using Aluminum Sec-Butoxide

To a reactor equipped with a mechanical stirrer, a reflux condenser, and a thermometer, aluminum sec-butoxide (140 g), MCPD (76.5 g) and toluene (154 g) were charged. The mixture was heated to 93° C. and a gentle reflux was maintained for 3 hours while 2-butanone and sec-butanol were formed. The reaction mixture was then cooled to room temperature followed by the addition of a 5% sodium hydroxide solution (220 mL) and toluene (200 mL). The organic phase was separated and concentrated to give KETOL. When KETOL is treated with a hydrochloric acid solution according to Example 2, BCE is formed in a yield of 92%.

Example 4. Preparation of 15-oxabicyclo[10.2.1]pentadec-1-ene and 4-hydroxy-cyclotetradecanone

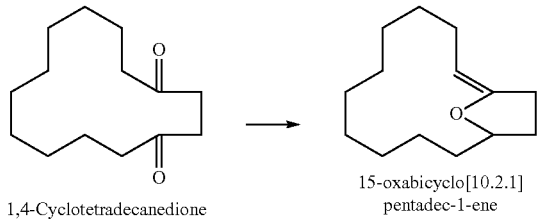 [SMILES: O=C1CCCCCCCCCCC(=O)CC1 ; C1=C2\CCC(CCCCCCCCC/1)O2]

15-Oxabicyclo[10.2.1]pentadec-1-ene was obtained from 1,4-cyclotetradecanedione according to the procedure described in example 1. Basic hydrolysis of the reaction mixture affords 4-hydroxy-cyclotetradecanone. See *J. Am. Chem. Soc.* 105, 5709-5710 (1983).

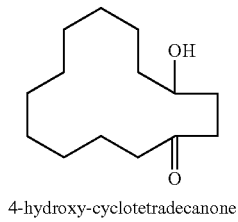 [SMILES: O=C1CCCCCCCCCCC(O)CC1]

Example 5. Preparation of 17-oxabicyclo[10.4.1]heptadec-12-ene and 6-hydroxycyclohexadecan-1-one

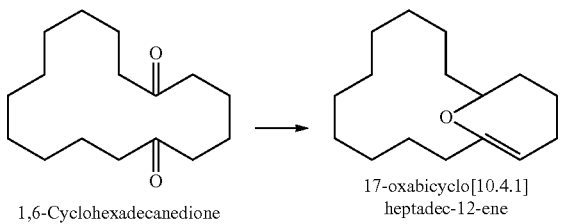 [SMILES: O=C1CCCCCCCCCCC(=O)CCCC1 ; C1=C2CCCCCCCCCCC(CCC1)O2]

Treatment of 1,6-cyclohexadecanedione with aluminum isopropoxide according to example 1 gives 17-oxabicyclo[10.4.1]heptadec-12-ene. Basic hydrolysis of the reaction mixture according to example 3 gives 6-hydroxycyclohexadecan-1-one.

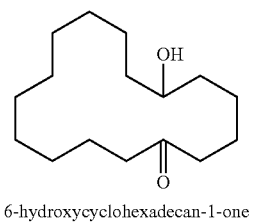 [SMILES: O=C1CCCCCCCCCCC(O)CCCC1]

Example 6. Preparation of 14-methyl-17-oxabicyclo[10.4.1]heptadec-12-ene and 15-methyl-17-oxabicyclo[10.4.1]heptadec-12-ene

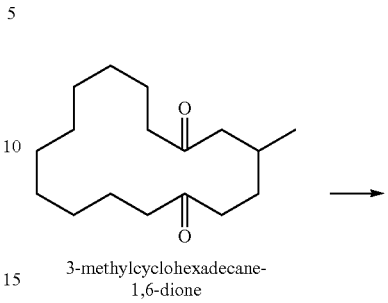

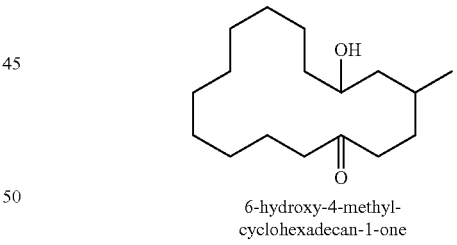

The reaction of 3-methylcyclohexadecane-1,6-dione with aluminum sec-butoxide according to example 2 gives an isomeric mixture of 14-methyl-17-oxabicyclo[10.4.1]-heptadec-12-ene and 15-methyl-17-oxabicyclo[10.4.1]heptadec-12-ene.

Treatment of the reaction mixture with 5% aqueous NaOH according to example 3 gives a mixture of 6-hydroxy-3-methylcyclohexadecan-1-one and 6-hydroxy-4-methylcyclohexadecan-1-one.

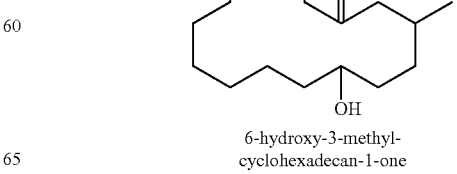

Example 7. Preparation of 14,15-dimethyl-17-oxabicyclo[10.4.1]heptadec-12-ene

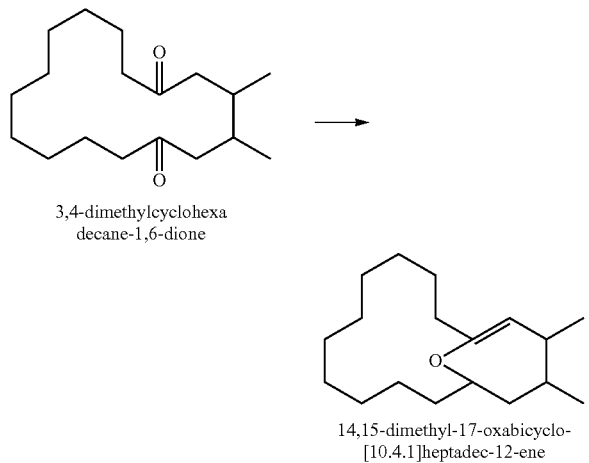

3,4-dimethylcyclohexadecane-1,6-dione 14,15-dimethyl-17-oxabicyclo-[10.4.1]heptadec-12-ene The reaction of 3,4-Dimethylcyclohexadecane-1,6-dione with Aluminum iso-propoxide according to example 1 gives 14,15-dimethyl-17-oxabicyclo[10.4.1]heptadec-12-ene. Work up of the reaction mixture with 5% aqueous NaOH according to example 3 gives 6-hydroxy-3,4-dimethylcyclohexadecan-1-one.

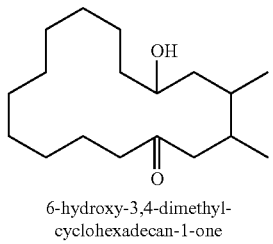 [SMILES: CC1CC(=O)CCCCCCCCCCC(O)CC1C]

6-hydroxy-3,4-dimethyl-cyclohexadecan-1-one

Comparative Examples

Comparative Example 1. Preparation of BCE by ruthenium-catalyzed hypochlorite oxidation of 3-methyl-1,5-cyclopentadecanediol (DIOL)

DIOL (50 g, 100%) was dissolved in 500 g of toluene. Ruthenium trichloride hydrate (0.4 g) was added and the mixture was stirred at room temperature. A solution of 6 wt % sodium hypochlorite (640 g) was added dropwise during 2.5 hours at such a rate as to keep the temperature at 25° C. to 33° C. When the addition was completed the stirring was stopped to allow phase separation. The lower aqueous phase was removed.

To the organic phase was added a 33% aqueous HCl solution (120 mL). The temperature was raised to 80° C. and stirred for 30 minutes. The organic phase was separated from the aqueous phase and was washed with water three times (400 mL each).

The wet organic phase was then distilled using Dean-Stark trap under an atmospheric pressure, during which the intermediate KETOL was converted to BCE. The toluene phase contained 72-75% BCE, 7-10% MCPD and 1% DIOL. The yield of BCE was 75-84%.

Comparative Example 2. Preparation of BCE Using Ru/Al(O)OH

Ru/Al(O)OH catalyst was prepared according to the procedure described by Won-Hee Kim, In Soo Park, and Jaiwook Park, Organic Letters, 8(12), 2543 (2006).

DIOL (0.25 g), Ru/Al(O)OH (0.25 g) and toluene (10 mL) were charged to a reaction vessel equipped with magnetic stirring. The stirred mixture was heated to 90° C. for 10 hours and then cooled to room temperature. According to GC analysis the reaction mixture contained 59.6% BCE, 3.7% MCPD, 1.8% KETOL and 25% unchanged DIOL.

Comparative Example 3. Preparation of BCE Using Shvo's Catalyst

To a reaction vessel equipped with magnetic stirring was charged DIOL (1 g), Shvo's catalyst (0.25 g, 5 mol %) and toluene (10 mL). The reaction mixture was stirred at 110° C. for 4 hours to obtain 69.3% BCE (2 isomers in ratio 4.6:1) and 16.6% MCPD.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%," which generally includes up to plus or minus 10% of the indicated number 50%.

All parts, percentages and proportions refer to herein and in the claims are by weight unless otherwise indicated.

The terms "include," "includes," and "including," are meant to be non-limiting.

The term "metalloid" as used herein refers to a chemical element that exhibits some properties of metals and some of nonmetals, for example, boron.

The term "alkyl," as used herein, means a linear or branched saturated hydrocarbon group containing from 1 to 20 carbon atoms, preferably 1 to 10 carbon atoms, sometimes more preferably 1 to 6 carbon atoms ("lower alkyl"), and sometimes more preferably 1 to 4 carbon atoms, which is connected with the rest of the molecular moiety through one or more single bonds. Representative examples of alkyl include, but are not limited to, methyl ("Me"), methylene (i.e., a bivalent methyl), ethyl ("Et"), ethylene, n-propyl, n-propylene, iso-propyl, iso-propylene, n-butyl, sec-butyl, iso-butyl, tert-butyl, n-butylene, sec-butylene, iso-butylene, tert-butylene, etc.

The term "halo" or "halogen" refers to F, Cl, Br, and I, preferably Cl, Br, and I.

The singular forms "a", "an", and "the" include plural references, and vice versa, unless the context clearly dictates otherwise.

All publications cited herein are incorporated by reference in their entirety for all purposes.

It should be understood that embodiments described herein should be considered as illustrative only, without limiting the scope of the invention. Descriptions of features or aspects within each embodiment should typically be considered as available for other similar features or aspects in other embodiments.

While several embodiments have been described in the Examples above, it will be understood by those of ordinary skill in the art that various changes in form and details may be made therein without departing from the spirit and scope of the disclosure as defined by the following claims.

What is claimed is:

1. A process for preparing 14-methyl-16-oxabicyclo[10.3.1]hexadec-12-ene, comprising:
   reacting 3-methyl-1,5-cyclopentadecanedione with an alkoxide of a metal or metalloid selected from the group consisting of sodium, magnesium, aluminum, boron, tin, zirconium and lanthanides in an inert organic solvent at an elevated temperature to form a reaction mixture; and
   treating the reaction mixture with aqueous mineral acid to obtain 14-methyl-16-oxabicyclo[10.3.1]hexadec-12-ene as a product.

2. The process according to claim 1, wherein the amount of metal or metalloid alkoxide is one or more molar equivalents relative to 3-methyl-1,5-cyclopentadecanedione.

3. The process according to claim 2, wherein the amount of the metal or metalloid alkoxide is in the range of 1 to 3 molar equivalents.

4. The process according to claim 2, wherein the amount of the metal or metalloid alkoxide is in the range of 1.5 to 1.8 molar equivalents.

5. The process according to claim 1, wherein the metal alkoxide is an aluminum alkoxide.

6. The process according to claim 1, wherein the metal alkoxide is aluminum sec-butoxide or aluminum iso-propoxide.

7. The process according to claim 1, wherein the inert organic solvent is selected from the group consisting of hexane, heptane, isooctane, toluene, xylene, dichloroethane, chlorobenzene, and 1,2-dichlorobenzene.

8. The process according to claim 1, wherein the inert organic solvent is toluene.

9. The process according to claim 1, wherein the elevated temperature is between 80° C. and 110° C.

10. The process according to claim 1, wherein the aqueous mineral acid is aqueous hydrochloric acid.

11. The process according to claim 1, wherein the aqueous mineral acid is hydrochloric acid at a concentration of 20-23%.

12. A process for preparing a compound of formula (II) and/or (III), comprising:

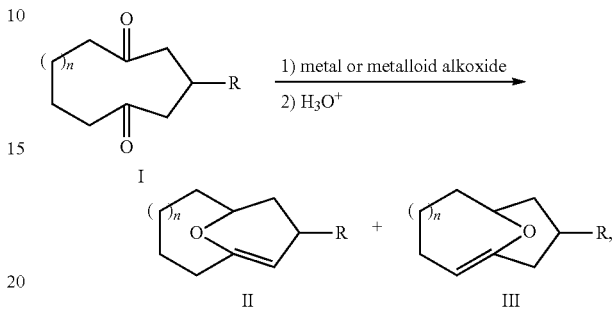

reacting a compound of formula (I) with an alkoxide of a metal or metalloid selected from the group consisting of sodium, magnesium, aluminum, boron, tin, zirconium and lanthanides, in an inert organic solvent and at an elevated temperature to form a reaction mixture;
treating the reaction mixture with aqueous mineral acid; and
isolating the compounds of formula (II) and (III),
wherein R is a $C_1$-$C_{10}$ alkyl; and
n is an integer selected from 4 to 10.

13. The process of claim 12, wherein R is $C_1$-$C_6$ alkyl.

14. The process according to claim 12, wherein n is 5, 6, or 7.

15. The process according to claim 12, wherein the metal alkoxide is an aluminum alkoxide.

16. The process according to claim 12, wherein the metal alkoxide is aluminum sec-butoxide or aluminum iso-propoxide.

17. The process according to claim 12, wherein the inert organic solvent is selected from the group consisting of hexane, heptane, isooctane, toluene, xylene, dichloroethane, chlorobenzene, and 1,2-dichlorobenzene.

18. The process according to claim 12, wherein the inert organic solvent is toluene.

19. The process according to claim 12, wherein the elevated temperature is between 80° C. and 110° C.

20. The process according to claim 12, wherein the mineral acid is hydrochloric acid.

* * * * *